(12) United States Patent
Masters

(10) Patent No.: US 7,887,488 B2
(45) Date of Patent: Feb. 15, 2011

(54) SYSTEMS AND METHODS FOR REDUCING NOISE IN AN IMAGING CATHETER SYSTEM

(75) Inventor: Donald Masters, Fremont, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 1072 days.

(21) Appl. No.: 11/559,019

(22) Filed: Nov. 13, 2006

(65) Prior Publication Data

US 2007/0167827 A1    Jul. 19, 2007

Related U.S. Application Data

(60) Provisional application No. 60/735,374, filed on Nov. 12, 2005.

(51) Int. Cl.
 *A61B 8/14* (2006.01)
(52) U.S. Cl. .................. 600/466; 600/459; 600/462
(58) Field of Classification Search ............. 600/466, 600/463, 437, 462; 607/156; 73/769
 See application file for complete search history.

(56) References Cited

U.S. PATENT DOCUMENTS

| | | | |
|---|---|---|---|
| 4,800,344 A | 1/1989 | Graham | |
| 5,115,814 A | 5/1992 | Griffith et al. | |
| 5,243,988 A | 9/1993 | Sieben et al. | |
| 5,361,768 A | 11/1994 | Webler et al. | |
| 5,368,037 A | 11/1994 | Eberle et al. | |
| 5,485,846 A | 1/1996 | Webler et al. | |
| 5,503,154 A | 4/1996 | Belef | |
| 5,592,942 A | 1/1997 | Webler et al. | |
| 5,759,153 A | 6/1998 | Webler et al. | |
| 5,807,253 A | 9/1998 | Dumoulin et al. | |
| 5,969,583 A * | 10/1999 | Hutchison | 333/181 |
| 6,013,030 A | 1/2000 | Webler et al. | |

(Continued)

FOREIGN PATENT DOCUMENTS

EP    0423895 A1    4/1991

(Continued)

OTHER PUBLICATIONS

Ladd et al., "Reduction of Resonant RF Heating in Intravascular Catheters Using Coaxial Chokes", Magnetic Resonance in Medicine, vol. 43, pp. 615-619, 2000.*

*Primary Examiner*—Long V Le
*Assistant Examiner*—Katherine L Fernandez
(74) *Attorney, Agent, or Firm*—Frommer Lawrence & Haug LLP; Bruce E. Black

(57) ABSTRACT

The present invention provides systems and methods for reducing noise in an imaging catheter system. In an embodiment, a catheter comprises an imaging transducer and a transmission line within the catheter to transmit signals to and from the transducer. To reduce noise caused by exposure of the transmission line to external interference, a choke balun is coupled to the transmission line. In another embodiment, the signal from a rotating imaging transducer of the catheter is coupled to a motor drive unit by a slip ring assembly. The transducer signal is passed through first and second transformers placed on opposite sides of the slip ring assembly to reduce noise from the slip ring assembly. In another embodiment, the catheter includes a position sensor to track the position of the catheter. The position sensor is coupled to a second choke balun to further reduce noise.

23 Claims, 8 Drawing Sheets

U.S. PATENT DOCUMENTS

| | | | |
|---|---|---|---|
| 6,063,292 A * | 5/2000 | Leung | 210/739 |
| 6,193,736 B1 | 2/2001 | Webler et al. | |
| 6,409,672 B2 | 6/2002 | Webler et al. | |
| 6,427,089 B1 * | 7/2002 | Knowlton | 607/101 |
| 6,908,434 B1 | 6/2005 | Jenkins et al. | |
| 6,996,432 B2 * | 2/2006 | Ostrovsky et al. | 600/424 |
| 7,077,808 B2 * | 7/2006 | Couvillon, Jr. | 600/466 |
| 7,232,433 B1 * | 6/2007 | Schlesinger et al. | 604/527 |
| 2003/0065267 A1 * | 4/2003 | Smith | 600/466 |
| 2004/0263172 A1 | 12/2004 | Gray | |

FOREIGN PATENT DOCUMENTS

| | | |
|---|---|---|
| EP | 0460711 A2 | 12/1991 |
| JP | 8033340 | 2/1996 |
| JP | 11276484 | 10/1999 |
| WO | WO 2006/003566 A1 | 6/2004 |
| WO | WO 2004/068947 A | 8/2004 |

* cited by examiner

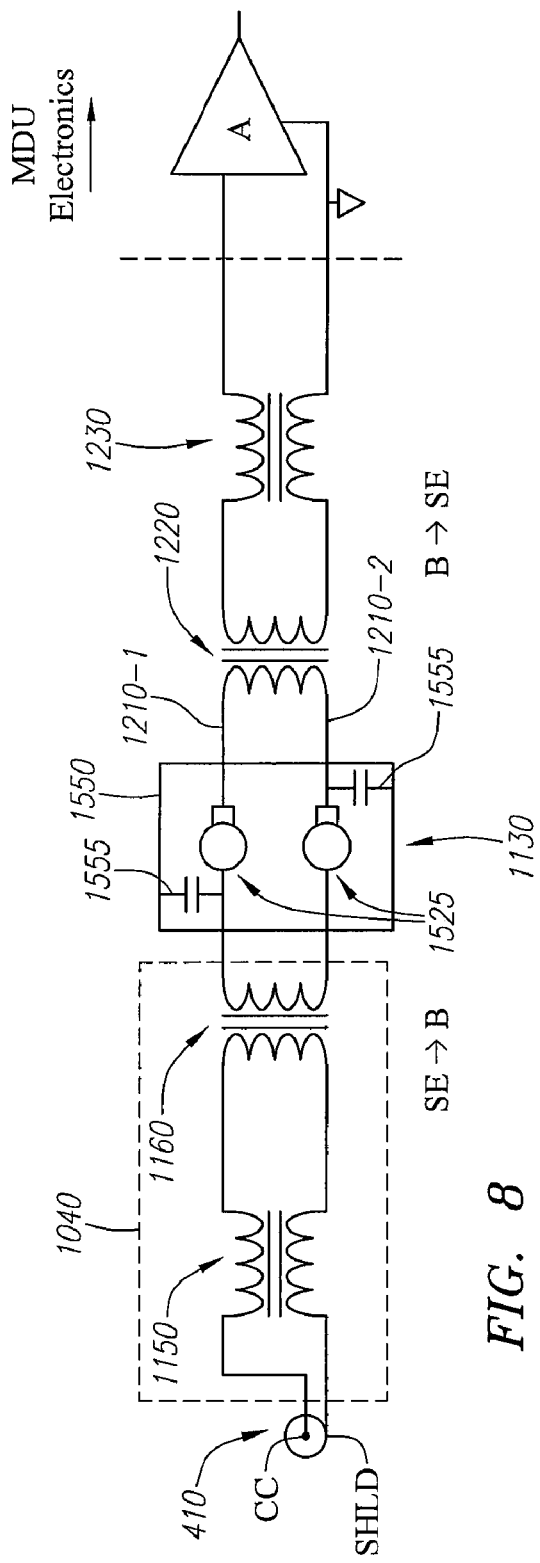
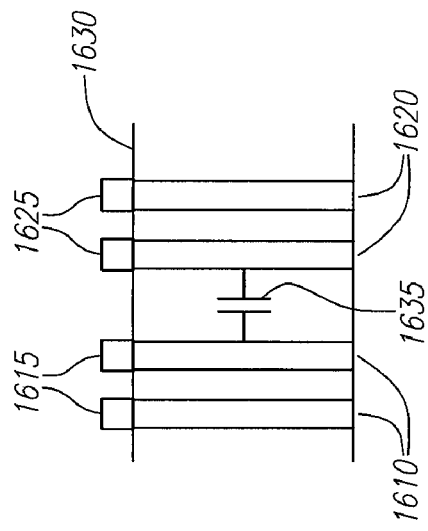
FIG. 8
FIG. 9

SYSTEMS AND METHODS FOR REDUCING NOISE IN AN IMAGING CATHETER SYSTEM

RELATED APPLICATION

This application claims the benefit of U.S. Provisional Patent Application Ser. No. 60/735,374, filed on Nov. 12, 2005.

FIELD OF THE INVENTION

The field of the invention relates to medical imaging systems, and more particularly to systems and methods for reducing noise in an imaging catheter system.

BACKGROUND OF THE INVENTION

Intraluminal, intracavity, intravascular, and intracardiac treatments and diagnosis of medical conditions utilizing minimally invasive procedures are effective tools in many areas of medical practice. These procedures are typically performed using imaging and treatment catheters that are inserted percutaneously into the body and into an accessible vessel of the vascular system at a site remote from the vessel or organ to be diagnosed and/or treated, such as the femoral artery. The catheter is then advanced through the vessels of the vascular system to the region of the body to be treated. The catheter may be equipped with an imaging device, typically an ultrasound imaging device, which is used to locate and diagnose a diseased portion of the body, such as a stenosed region of an artery. For example, U.S. Pat. No. 5,368,035, issued to Hamm et al., the disclosure of which is incorporated herein by reference, describes a catheter having an intravascular ultrasound imaging transducer.

FIG. 1 shows an example of an imaging transducer assembly 1 known in the art. The imaging transducer 1 is typically within the lumen 60 of a guidewire (partially shown), having an outer tubular wall member 5. The imaging transducer assembly 1 includes a coaxial cable 110, having a center conductor wire and an outer shield wire (not shown). A conductive wire, having a diameter of approximately 500 microns, is wrapped around the coaxial cable 110, forming a coil, which functions as a drive shaft 10. Connected to the distal end of the drive shaft 10 is a stainless steel housing 20, which serves to reinforce the structure of the imaging transducer assembly 1. Surrounding the coaxial cable 110, within the housing 20 is a silver epoxy 30, a conductive material. Thus, the housing 20 is electrically coupled to the shield wire of the coaxial cable 110 via the epoxy 30. On the distal end of the silver epoxy 140 is an insulating substance, a non-conductive epoxy 35.

On the distal end of the non-conductive epoxy 35 is a layer of piezoelectric crystal ("PZT") 80, "sandwiched" between a conductive acoustic lens 70 and a conductive backing material 90, formed from an acoustically absorbent material (e.g., an epoxy substrate having tungsten particles). The acoustic lens 70 is electrically coupled with the center conductor wire of the coaxial cable 110 via a connector 40 that is insulated from the silver epoxy 30 and the backing material 90 by the non-conductive epoxy 35. The backing material 90 is connected to the steel housing 20. It is desirable for the imaging transducer assembly 1 to be surrounded by a sonolucent media. Thus, the lumen 60 of the guidewire is also filled with saline around the assembly 1. The driveshaft 10, the housing 20, and the acoustic lens 70 are exposed to the saline. During operation, the PZT layer 80 is electrically excited by both the backing material 90 and the acoustic lens 70. The backing material 90 receives its charge from the shield wire 140 of the coaxial cable 110 via the silver epoxy 30 and the steel housing 30, and the acoustic lens 70, which may also be silver epoxy, receives its charge from the center conductor wire 120 of the coaxial cable 110 via the connector 40, which may be silver epoxy as well.

In some instances, it may be desirable to be able to obtain not only the cross-sectional image of a blood vessel, but also information such as the three-dimensional longitudinal profile of the same blood vessel. One approach in obtaining such additional information is to use a medical positioning system, which is generally known in the art. Turning to FIG. 2a, a prior art medical positioning system 240 is illustrated. The system 240 generally includes a plurality of transmitter and/or receiver nodes 250 that may be arranged around a patient. For instance, the nodes 250 may be arranged on a framework of towers that surround a patient. The system 240 further includes one or more sensors 260, which are configured to send and/or receive electromagnetic, or electromechanical, signals to and/or from the transmitter/receiver nodes 250.

A sensor 260, coupled with a guidewire (partially shown), may be placed within the blood vessel of a patient's body. The signals exchanged between the sensor 260 and the nodes 250 function as navigational signals which, as can be appreciated by one of ordinary skill in the art, may be used to determine the position of the sensor 260 within the patient's body. In other words, the sensor 260 transmits navigational signals to the nodes 250, and a processor (not shown) coupled with the nodes 250 determines the position of the sensor 260 based on the signals received by the nodes 250. Alternatively, or in addition, the nodes 250 may send navigational signals to the sensor 260, and a processor (not shown) coupled with the sensor 260 determines the position of the sensor 260 within the patient's body based on the signals sent by the nodes 250. The medical positioning system 240 can track and record the position of the sensor 260 as it is moved throughout a patient's blood vessel, thus providing a longitudinal profile of the blood vessel.

As is known in the art, a sensor of a medical positioning system may be combined with an imaging transducer to form a transducer/sensor assembly 300. Turning to FIG. 2b, a cross-sectional side view of an example transducer/sensor assembly 300 is shown in a lumen 305 of the distal portion of a guidewire or catheter assembly (partially shown) having an outer tubular wall 301. The transducer/sensor assembly 300 includes an imaging transducer 340, such as that described above, and a sensor 320 of a medical positioning system. The "antenna" portion of the sensor 320 is an insulated conductive wire 325. The wire 325 may also have magnetic qualities. The wire 325 is tightly wrapped around a portion of the distal end of the coaxial cable 410 and non-conductive epoxy 330, and is also tightly wrapped around the distal end of the drive shaft 310, forming a second coil shape. The second coil shape desirably provides an inductance for the antenna portion of the sensor 320 when charged to increase its ability to send and receive electromagnetic signals. A more detailed description of a catheter having a combined transducer/sensor assembly is provided in U.S. patent application Ser. No. 10/401,901, filed on Mar. 28, 2003, which is hereby incorporated by reference in its entirety.

The environment within which the imaging catheter operates typically includes other electronic devices, such as an electrocardiogram ("EKG") system or other monitors, which are situated fairly close to the catheter so the technician has convenient access to all the devices. However, each of these devices generate an electromagnetic field, and if they are situated sufficiently close, the respective fields can cause signal distortion in other devices. Accordingly, an improved imaging system is desirable.

SUMMARY OF THE INVENTION

The present invention provides systems and methods for reducing noise in an imaging catheter system. In an embodiment, a catheter comprises an imaging transducer and a transmission line within the catheter to transmit signals to and from the transducer. To reduce noise caused by exposure of the transmission line to external interference, a choke balun is coupled to the proximal end of the transmission line. The choke balun passes the desired transducer signal while attenuating noise introduced in the transmission line. In an embodiment, the transmission line comprises a coaxial cable having a center conductor surrounded by a shield. In this embodiment, the choke balun attenuates unwanted current induced in the shield of the coaxial cable by external electric fields from neighboring devices.

In another embodiment, the signal from a rotating imaging transducer of the catheter is coupled to a motor drive unit by a slip ring assembly. In this embodiment, the transducer signal is passed through first and second transformers placed on opposite sides of the slip ring assembly to reduced noise from the slip ring assembly. The slip ring assembly preferably comprises a mercury slip ring assembly.

In another embodiment, a balun is coupled to the second transducer. This balun may be used to convert the balanced transducer signal into a single-ended signal and/or to reject common-mode noise to further improve the signal.

In another embodiment, the catheter includes a position sensor to track the position of the catheter. The position sensor is coupled to a second transmission line within the catheter to transmit signals to and from the position sensor. To further reduce noise, a second choke balun is coupled to the proximal end of the second transmission line.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the present inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 8 is a circuit diagram of a noise reduction circuit in accordance with an embodiment of the present invention.

FIG. 9 is a diagram of an example slip ring assembly in accordance with an embodiment of the present invention.

DETAILED DESCRIPTION OF THE PREFERRED EMBODIMENTS

Figure 3:
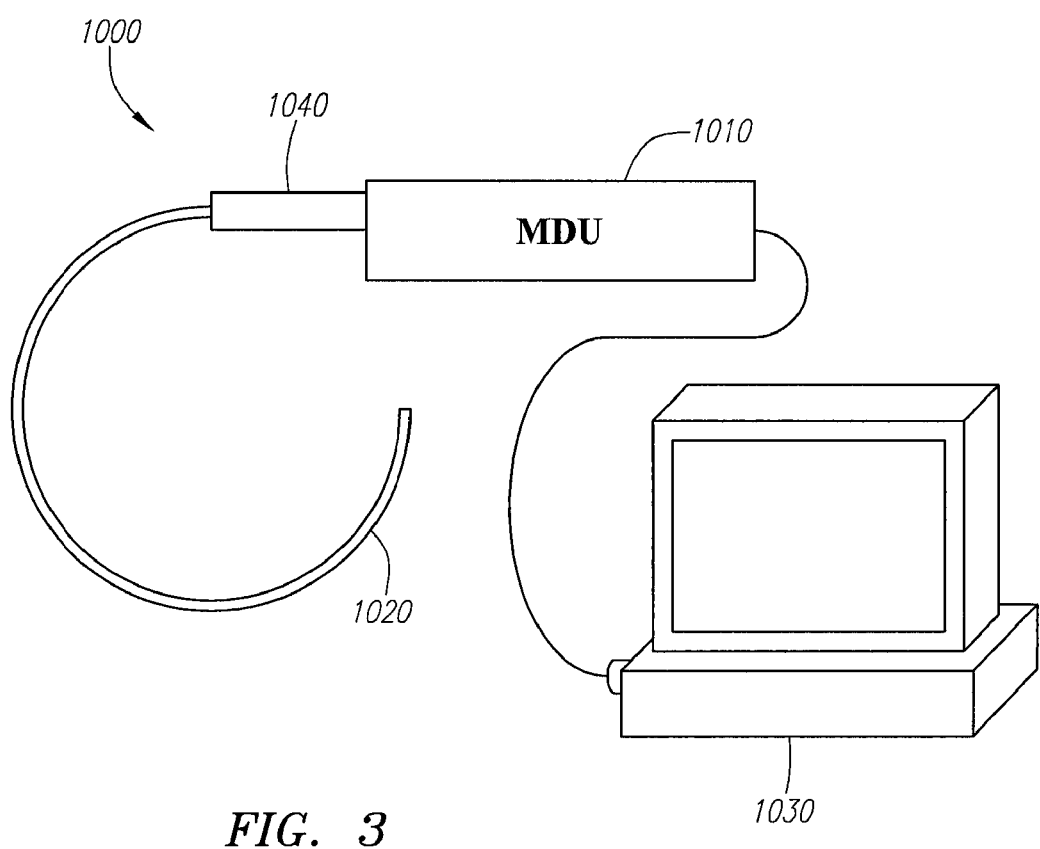
FIG. 3 is a diagram of a medical imaging system in accordance with a preferred embodiment of the present invention.

Turning to FIG. 3, an illustration of a medical imaging system 1000 in accordance with a preferred embodiment is shown. The system 1000 comprises an imaging catheter or guidewire 1020, such as those described above, which is adapted to be inserted into a lumen of the body and preferably within the vascular system of the body. The imaging catheter 1020 detachably connects to a motor drive unit ("MDU") 1010 via a hub 1040. The MDU 1010 is electrically coupled to a signal processing console 1030. The MDU 1010 includes a motor (not shown) that couples to the drive shaft of the catheter 1020 for rotating the transducer. A more detailed description of the MDU is provided in U.S. Pat. No. 6,261,246, filed on Sep. 28, 1998, which is hereby incorporated by reference in its entirety.

Figure 1:
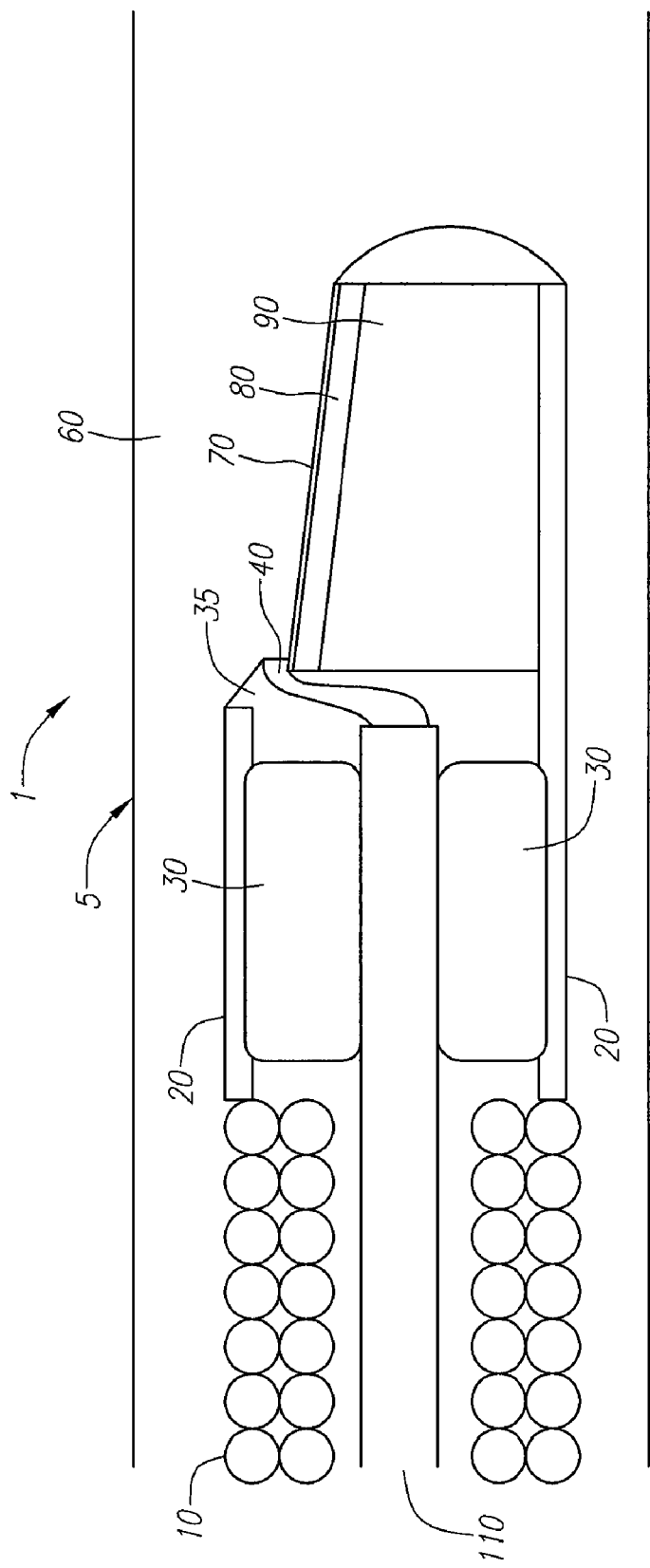
FIG. 1a is a cross-sectional side view of an imaging transducer assembly known in the art.
Figure 2A:
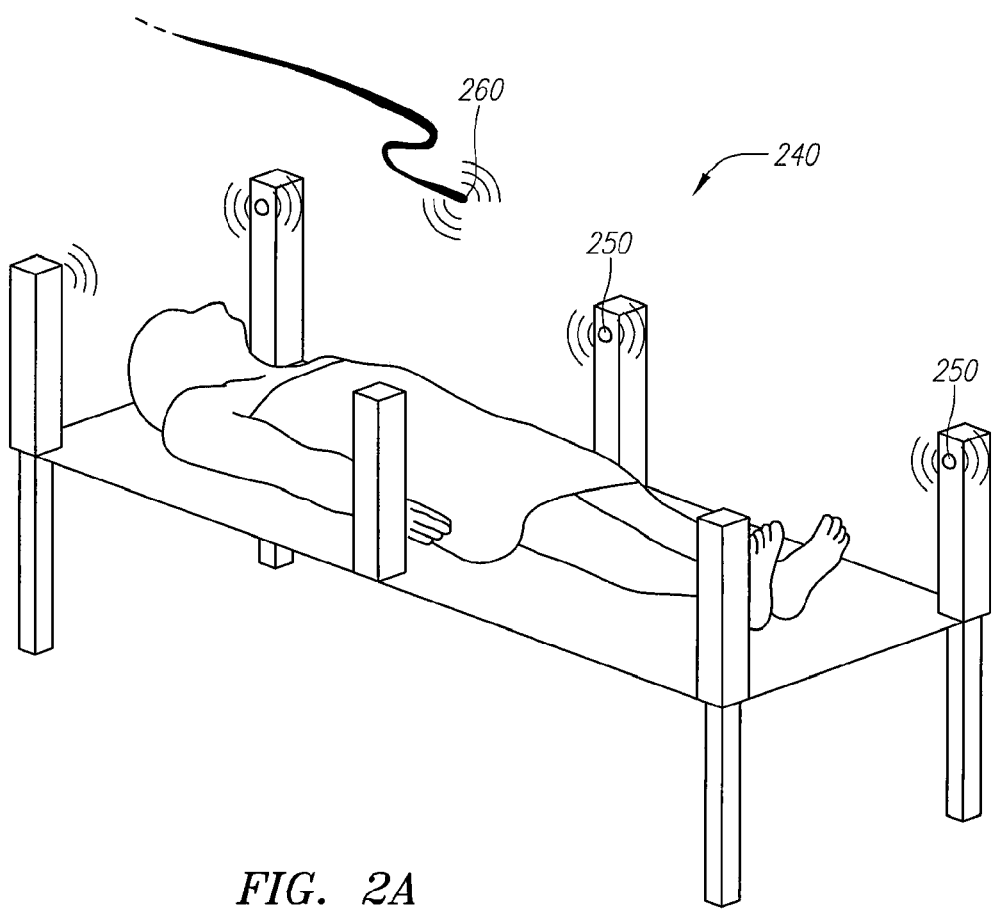
FIG. 2a is an illustration of a prior art medical positioning system.
Figure 2B:
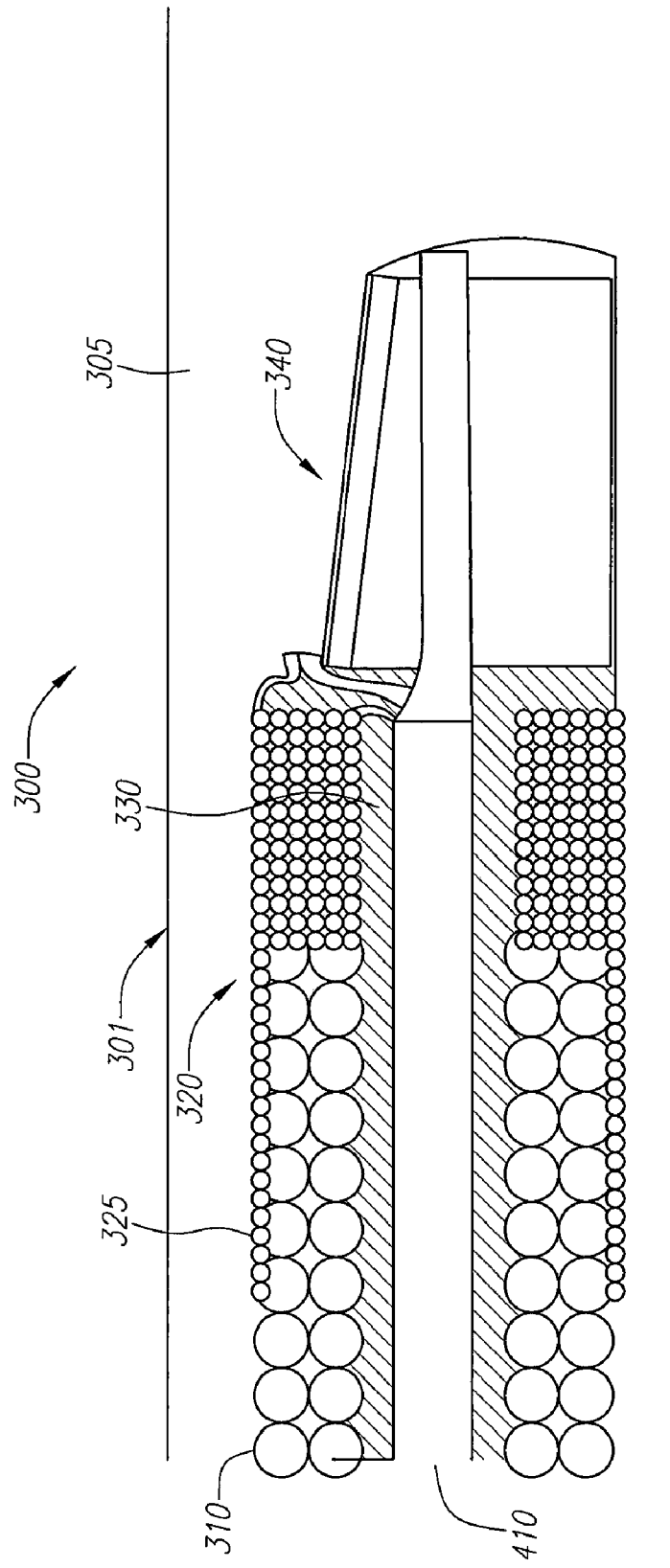
FIG. 2b is cross-sectional side view of an imaging transducer assembly known in the art.
Figure 4:
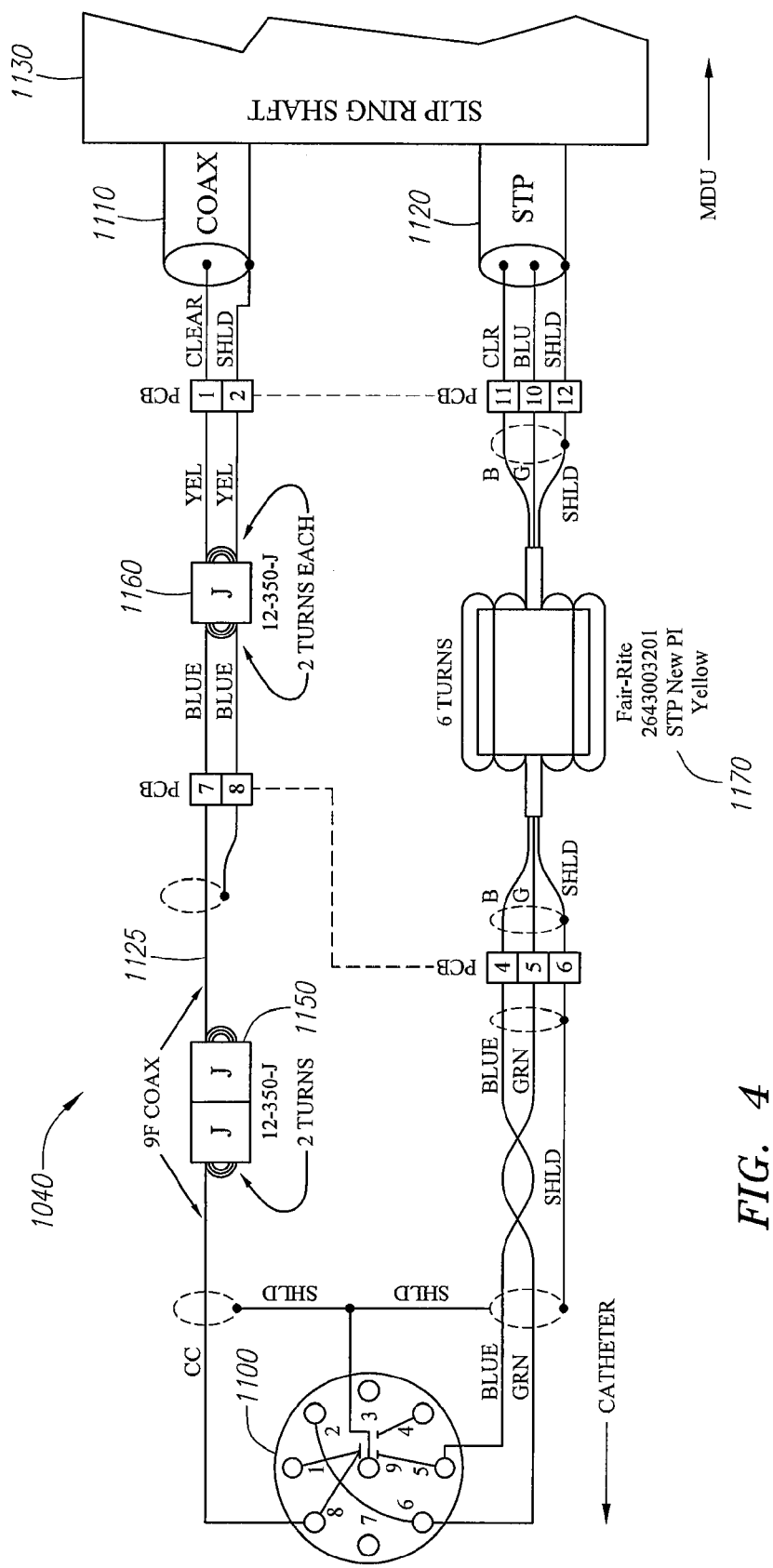
FIG. 4 is a diagram of a circuit in accordance with a preferred embodiment of the present invention.

As mentioned above, in a typical operating environment, other electronic devices are situated near the imaging system 1000, and their respective electromagnetic fields may introduce distortion into the signal lines of the imaging system 1000. One approach to address this problem is illustrated in FIG. 4, which shows a diagram of the preferred circuitry for the hub 1040. In this embodiment, the hub 1040 is configured to be connected to an imaging catheter 1020 having both a positioning sensor and an imaging transducer such as the transducer/sensor assembly 300 shown in FIG. 2b. The hub 1040 connects to the imaging catheter 1020 through a 9-pin interface 1100. As will be appreciated by one of ordinary skill in the art, a catheter 1020 with a transducer/sensor assembly 300 typically includes two distinct transmission lines (not shown), a first transmission line for signals from the imaging transducer 340, and a second transmission line for signals from the position sensor 320. Generally, because of the nature of the data signals, e.g., frequency ranges, the first and second transmission lines are of different types. The first transmission line, which is coupled to the transducer 340, is a coaxial cable, and the second transmission line, which is coupled to the position sensor 320, is a twisted pair line. The hub 1040 includes a coax line 1110, which is coupled to the first transmission line for the transducer 340, and a shielded twisted pair line 1120, which is coupled to the second transmission line for the position sensor 320.

The center conductor CC of a coax line 1125 is connected to pin 8 of the catheter interface 1100 and the shield SHLD of the coax line 1125 is connected to pin 9 of catheter interface 1100. The coax line 1125 is wound around two juxtaposed ferrite cores J to form a first choke balun 1150. The first choke balun 1150 prevents signal distortion caused by electronic fields from other devices or the signal processing equipment 1030, as explained further below. The center conductor CC and shield SHLD of the coax line 1125 are further coupled to a first printed circuit board PCB. The first PCB includes a third ferrite core J with a first wire BLUE and a second wire YEL wound around the third ferrite core J to form a first RF transformer 1160. The first wire BLUE is connected at opposite ends to the center conductor CC and shield SHLD of coax line 1125. The second wire YEL is connected at opposite ends to the center conductor and shield of coax line 1110. The hub circuitry shown in FIG. 4 is rotated with the imaging transducer 340 and coaxial cable of the catheter by the drive shaft of the MDU 1010.

Figure 5:
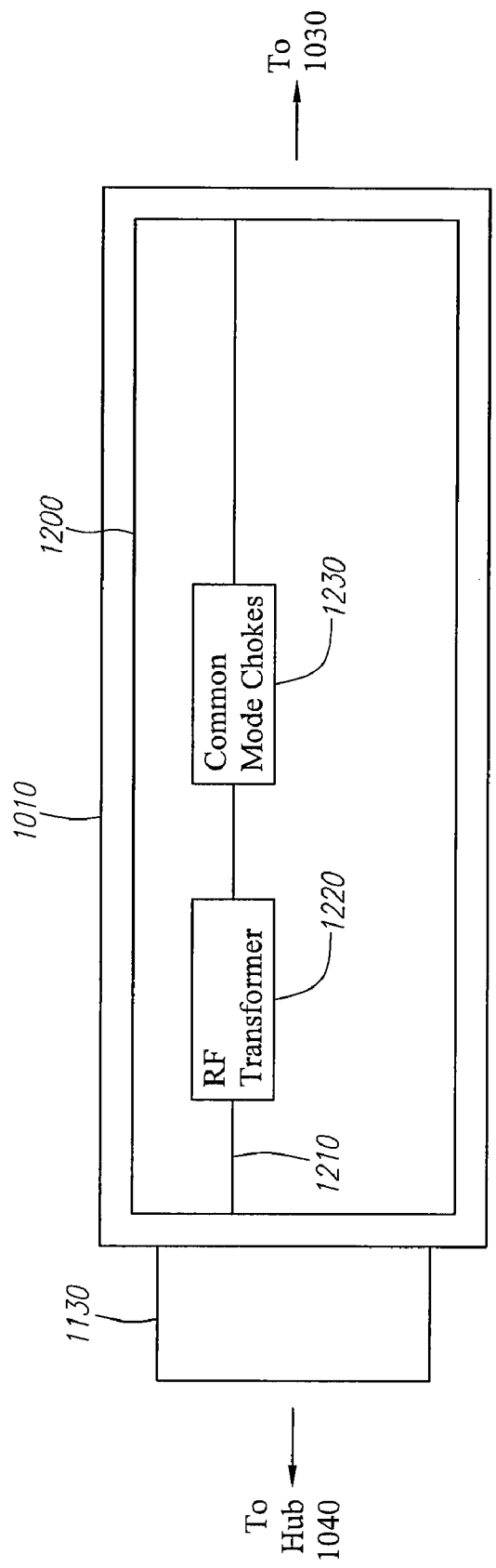
FIG. 5 is a diagram of a circuit in accordance with a preferred embodiment of the present invention.
Figure 7:
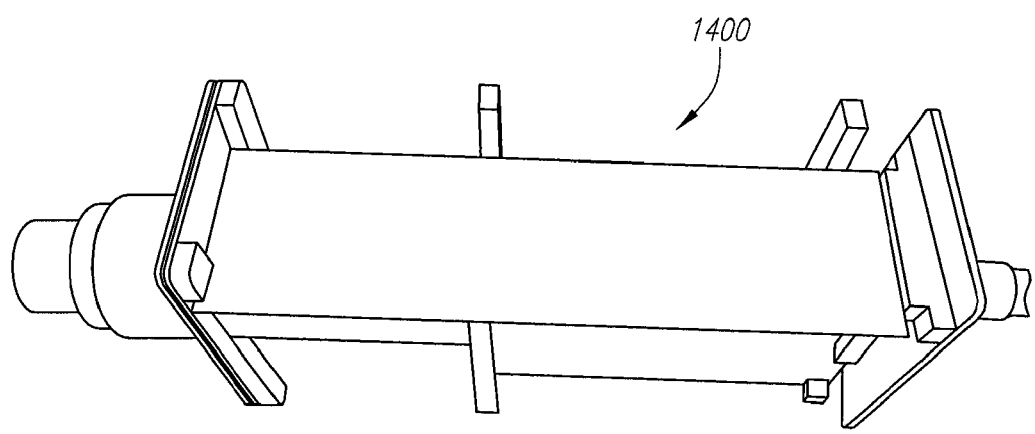
FIG. 7 is a photograph of a printed circuit board in accordance with a preferred embodiment of the present invention.

Turning to FIG. 5, the transducer data signal in coax line 1110 travels through a slip ring assembly 1130 to a transducer line 1210 defined in a second printed circuit board (PCB) 1200 within the MDU 1010. The second printed circuit board 1200 includes circuitry for controlling the transmission and reception of data signals as well as for controlling the actual motor (not shown) within the MDU 1010. An actual photograph of the second printed circuit board 1400 is shown in FIG. 7. The slip ring assembly 1130 electrically couples signals from the rotating circuitry of the hub 1040 to the circuitry 1200 of the MDU 1010. To do this, the slip ring assembly 1130 includes ring conductors that are connected to the circuitry of the hub 1040 and are disposed on a shaft that rotates with the hub 1040. The slip ring assembly also includes fixed conductors that make electrical contact with the rotating ring conductors and are connected to the circuitry 1200 of the MDU 1010.

Figure 6:
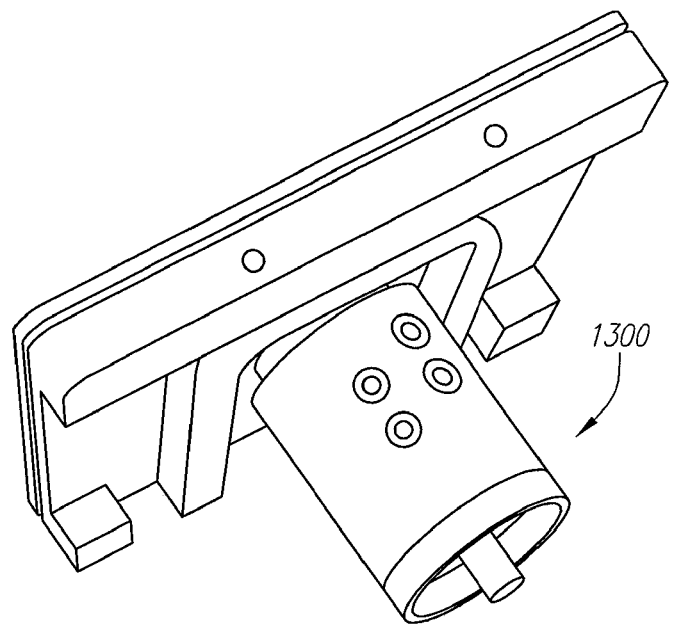
FIG. 6 is a photograph of a slip ring assembly in accordance with a preferred embodiment of the present invention.

The slip ring assembly 1130 provides an interface between the hub 1040 and the MDU 1010, which rotates the hub 1040 and the imaging transducer 340 within the catheter 1020. Traditional slip ring assembly provide a mechanical connection between a hub and a rotating motor; however, mechanical connections typically introduce noise and high impedance circuits, which can cause problems for transmitting ultrasound signals and higher frequency signals in general, as will be appreciated by one of ordinary skill in the art. One solution is to provide a mercury slip ring assembly 1130. The mercury slip ring assembly 1130 provides pockets of conductive liquid mercury between the ring conductors and fixed conductors. Thus, the transmission of data between the conductors is passed through the liquid mercury, which results in a connection with substantially less impedance than a traditional mechanical connection and also less noise. A photograph of the outside casing of an actual mercury slip ring assembly 1300 is shown in FIG. 6. Other embodiments include a brush ring slip assembly, wherein conductive bristles are utilized between two connectors.

The second PCB 1200 within the MDU 1010 includes a second RF transformer 1220 coupled to the transducer line 1210. The second RF transformer 1220 provides a number of features. For example, the second RF transformer 1220 electrically isolates the electrical signal of the catheter 1020 from the system's 1000 ground. This results in desirable "patient isolation" known in the art. The RF transformer 1220 is preferably positioned over an area of fiber glass. The second PCB 1200 may also include one or more baluns 1230 coupled to the second RF transformer 1220 and the electronics of the MDU (not shown).

Operation of the noise reduction circuitry for the transducer signal path will now be described with reference to FIG. 8, which shows a simplified circuit diagram of the noise reduction circuitry.

As mentioned above, signals from the imaging transducer 340 are transmitted through the catheter via a coaxial cable 410 comprising a center conductor wire CC and a shield SHLD surrounding the center conductor wire CC. The coaxial cable 410 is coupled at one end to the imaging transducer 340 and at the other end to the noise reduction circuitry. The transducer signal in the coaxial cable 410 causes a current to flow in the center conductor CC and a current of equal magnitude to flow in the opposite direction in the shield SHLD. Because the sum of the currents of the transducer signal is zero, the transducer signal is able to pass through the first choke balun 1150 with little or no attenuation. The shield SHLD of the coaxial cable also acts as an antenna that picks up external interference from neighboring devices. Electric fields from these devices induce an unwanted current in the outer surface of the shield SHLD causing signal distortion. The first choke balun 1150 presents a high impedance to this unwanted shield current, thereby attenuating the unwanted shield current and reducing the resulting signal distortion. The impedance seen by the unwanted shield current can be increased by increasing the number of turns that the coax line 1125 is wound around the ferrite cores J forming the first choke balun 1150.

After passing through the first choke balun 1150, the transducer signal is converted into a balanced signal by the first RF transformer 1160. The balanced transducer signal comprises two inverse signals that travel on separate lines 1210-1 and 1210-2 of transmission line 1210. The balanced transducer signal is coupled to the second RF transformer 1220 by a pair of slip rings 1525 of the slip ring assembly 1130. The balanced transducer signal facilitates the rejection of common-mode noise introduced into the signal by the slip ring assembly 1130, as explained below.

The slip ring assembly may include an outer casing 1550 and/or other part that pick ups external interference from neighboring devices. This external interference may then be introduced into the balanced transducer signal by capacitive coupling between the slip rings 1525 and the outer casing 1550. This capacitive coupling is represented graphically by capacitors 1555 in FIG. 8. Assuming that the external interference affects both inverse signals of the balanced transducer signal equally, the external interference is suppressed by the second RF transformer 1220. This is because the second RF transformer 1220 suppresses common-mode noise, i.e., noise that is common to both inverse signals of the balanced signal. Thus, the first and second transformers 1160 and 1220 placed on opposite sides of the slip ring assembly 1130 provide a balanced transducer signal and act to suppress noise introduced by the slip ring assembly 1130.

After passing the second transformer 1220, the transducer signal may be passed through another balun 1230. This balun 1230 may be used to covert the balanced signal into a single-ended signal for input to the electronics of the MDU 1010. FIG. 8 shows an example in which the single-ended signal is inputted to an amplifier of the MDU 1010 for amplification and further processing. The balun 1230 may also include one or more common-mode rejection choke baluns to improve the signal by further rejecting common mode signals.

Turning back to FIG. 4, the noise reduction circuitry further comprises a twisted pair line 1120 coupled to the twisted pair line of the catheter, which carries the signal for the position sensor 320. A first line BLUE and second line GRN of the twisted pair line are coupled to pins 5 and 6 of the catheter interface 1100, respectively. The twisted pair line 1120 further shares the shield SHLD of the coaxial line 1110 to provide a shielded twisted pair line. The shielded twisted pair line 1120 is coupled to the first PCB and is wound six times around a fourth ferrite core forming a second choke balun 1170 within the hub 1040. Like the first choke balun 1150, the second choke balun 1170 prevents signal distortion introduced into the twisted pair line by external interferences from neighboring electronic devices or the signal processing equipment 1030. The second choke balun 1170 also suppresses unwanted shield current induced in the shield SHLD of the coaxial cable of the catheter and introduced into the shielded twisted pair line. The shielded twisted pair line 1120 is coupled to the signal processing equipment 1030 by the slip ring assembly 1130. The noise reduction circuitry for the position sensor is not needed for a catheter that does not use a position sensor.

FIG. 9 shows a diagram of an example slip ring assembly 1130. The example slip ring includes four ring conductors 1610 and 1620 on the shaft 1630 of the MDU and four corresponding fixed conductors 1615 and 1625, respectively. In a mercury slip ring assembly 1130, each ring conductor is electrically coupled to the corresponding fixed conductor by liquid mercury. Two of the ring conductors 1610 are used to couple the transducer signal to the MDU 1010 while the other two ring conductors 1620 are used to couple the position sensor signal to the MDU 1010. The proximity of the ring conductors 1610 and 1620 to each other may result in capacitive coupling between the ring conductors, which is represented graphically by capacitor 1635 in FIG. 9. Because the transducer signal and the position sensor signal typically operate in much difference frequency ranges, they do not interfere with each other. However, the shielded twisted pair line may carry external interference within the frequency range of the transducer signal that can be introduced into the transducer signal by the capacitive coupling 1635 between the ring conductors 1610 and 1620. The second choke balun 1170 prevents this by suppressing external interference, e.g., induced shield current, in the shielded twisted pair line 1120 before it reaches the slip ring assembly 1130.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. For example, this invention is particularly suited for applications involving medical imaging devices, but can be used on any design involving imaging devices in general. As a further example, each feature of one embodiment can be mixed and matched with other features shown in other embodiments. Additionally and obviously, features may be added or subtracted as desired. For example, though the embodiment described includes a transducer/sensor assembly 300, a device having only a transducer 340 (and the corresponding circuitry) or a device having only a sensor 320 (and the corresponding circuitry) can still fall within the scope of the invention. Accordingly, the invention is not to be restricted except in light of the attached claims and their equivalents.

What is claimed is:

1. A catheter system, comprising:
   a catheter having distal and proximal ends;
   an ultrasound transducer located towards the distal end of the catheter;
   a transmission line within the catheter and coupled at one end to the ultrasound transducer, the transmission line having a center conductor wire and a shield surrounding the center conductor wire;
   a choke balun coupled to the other end of the transmission line to reduce unwanted current generated in the shield;
   a first transformer coupled to the choke balun;
   a second transformer; and
   a slip ring coupled between the first and second transformers.

2. The catheter system of claim 1, wherein the transmission line comprises a coaxial cable.

3. The catheter system of claim 1, wherein the choke balun comprises one or more ferrite cores and a coaxial cable wound around the one or more ferrite cores.

4. The catheter system of claim 1, wherein the slip ring comprises a mercury slip ring.

5. The catheter system of claim 1, further comprising a second balun coupled to the second transformer.

6. The catheter system of claim 1, further comprising a rotatable hub connectable to the transmission line of the catheter, wherein the choke balun and first transformer are housed within the rotatable hub.

7. The catheter system of claim 6, further comprising a motor drive unit rotatably coupled to the hub and configured to rotate the hub.

8. The catheter system of claim 7, wherein the second transformer is housed within the motor drive unit.

9. The catheter system of claim 1, further comprising:
   a position sensor located towards the distal end of the catheter;
   a second transmission line within the catheter and coupled at one end to the position sensor; and
   a second choke balun coupled to the other end of the second transmission line.

10. The catheter system of claim 9, wherein the second choke balun comprises a ferrite core and a shielded transmission line wound around the ferrite core.

11. The catheter system of claim 10, wherein the transmission line coupled to the ultrasound transducer is a the first transmission line and the second transmission line includes a shield coupled to the shield of the first transmission line.

12. The catheter system of claim 11, wherein the first transmission line comprises a coaxial cable.

13. The catheter system of claim 11, wherein the second transmission line comprises a shielded twisted pair line.

14. A catheter system, comprising:
   a catheter having distal and proximal ends;
   a transducer located towards the distal end of the catheter;
   a transmission line within the catheter and coupled at one end to the transducer;
   a first transformer coupled to the other end of the transmission line;
   a second transformer; and
   a slip ring coupled between the first and second transformers.

15. The catheter system of claim 14, wherein the transmission line comprises a coaxial cable.

16. The catheter system of claim 14, wherein the transducer comprises an ultrasound transducer.

17. The catheter system of claim 14, wherein the slip ring comprises a mercury slip ring.

18. The catheter system of claim 14, further comprising a balun coupled to the second transformer.

19. The catheter system of claim 18, wherein the balun is configured to convert a balanced signal from the second transformer into a single-ended signal.

20. The catheter system of claim 14, further comprising a rotatable hub connectable to the transmission line of the catheter, wherein the first transformer is housed within the rotatable hub.

21. The catheter system of claim 20, further comprising a motor drive unit rotatably coupled to the hub and configured to rotate the hub.

22. The catheter system of claim 21, wherein the second transformer is housed within the motor drive unit.

23. The catheter system of claim 14, wherein the first transformer is configured to convert a single-ended signal from the transmission line into a balanced signal.

* * * * *